United States Patent
Wu et al.

(10) Patent No.: US 7,867,176 B2
(45) Date of Patent: Jan. 11, 2011

(54) VARIABLE STIFFNESS GUIDEWIRE

(75) Inventors: Mina Wu, Durham, NC (US); Hikmat Hojeibane, Princeton, NJ (US)

(73) Assignee: Cordis Corporation, Miami Lakes, FL (US)

( * ) Notice: Subject to any disclaimer, the term of this patent is extended or adjusted under 35 U.S.C. 154(b) by 751 days.

(21) Appl. No.: 11/318,825

(22) Filed: Dec. 27, 2005

(65) Prior Publication Data

US 2007/0149951 A1 Jun. 28, 2007

(51) Int. Cl.
*A61B 5/00* (2006.01)
(52) U.S. Cl. ........................ 600/585; 604/526
(58) Field of Classification Search ............... 600/585; 604/526
See application file for complete search history.

(56) References Cited

U.S. PATENT DOCUMENTS

| | | | |
|---|---|---|---|
| 3,452,742 A | | 7/1969 | Muller |
| 3,749,085 A | * | 7/1973 | Willson et al. ............... 600/570 |
| 3,854,473 A | | 12/1974 | Matsuo |
| 4,215,703 A | | 8/1980 | Willson |
| 4,271,845 A | * | 6/1981 | Chikashige et al. ......... 600/569 |
| 4,390,599 A | | 6/1983 | Broyles |
| 4,456,017 A | | 6/1984 | Miles |
| 4,555,839 A | * | 12/1985 | Thurber .................... 29/450 |
| 4,864,824 A | | 9/1989 | Gabriel et al. |
| 4,981,756 A | | 1/1991 | Rhandhawa |
| 5,061,914 A | | 10/1991 | Busch et al. |
| 5,082,359 A | | 1/1992 | Kirkpatrick |
| 5,120,488 A | * | 6/1992 | Borrman et al. .............. 376/203 |
| 5,178,957 A | | 1/1993 | Kolpe et al. |
| 5,197,978 A | | 3/1993 | Hess |
| 5,288,230 A | | 2/1994 | Nikutowski et al. |
| 5,334,216 A | | 8/1994 | Vidal et al. |
| 5,360,397 A | | 11/1994 | Pinchuk |
| 5,376,109 A | | 12/1994 | Lindegren et al. |

(Continued)

FOREIGN PATENT DOCUMENTS

EP 0847733 A1 12/1997

(Continued)

OTHER PUBLICATIONS

Boston Scientific, Fathom Steerable Guidwire, Printout Dec. 9, 2005, bostonscientific.com.

(Continued)

*Primary Examiner*—Max Hindenburg
*Assistant Examiner*—Renee Danega
(74) *Attorney, Agent, or Firm*—Cook Alex Ltd.

(57) ABSTRACT

A guidewire navigable through body vessels of a human subject for delivery of a catheter or the like is provided. The guidewire has a tube which receives a corewire that protrudes beyond a distal portion of the tube. The protruding portion of the corewire is surrounded by a spring and shapeable into a curve or arc. The cross-sectional shape of the spring may be varied in order to promote bending flexibility and curvature or to favor curvature of a chosen type. The corewire is axially movable with respect to the tube, which compresses or stretches the spring to change the stiffness of the spring. The tube has a proximal portion comprised of a relatively rigid material, such as stainless steel, while a distal portion is comprised of a more flexible material, such as a nitinol.

27 Claims, 2 Drawing Sheets

U.S. PATENT DOCUMENTS

| | | | |
|---|---|---|---|
| 5,403,700 | A | 4/1995 | Heller et al. |
| 5,404,887 | A * | 4/1995 | Prather ...................... 600/585 |
| 5,543,019 | A | 8/1996 | Lee et al. |
| 5,607,463 | A | 3/1997 | Schwartz et al. |
| 5,629,077 | A | 5/1997 | Turnlund et al. |
| 5,656,036 | A | 8/1997 | Palmaz |
| 5,669,977 | A | 9/1997 | Shufflebotham et al. |
| 5,673,707 | A | 10/1997 | Chandrasekaran |
| 5,681,575 | A | 10/1997 | Burrell et al. |
| 5,685,961 | A | 11/1997 | Pourrezaei et al. |
| 5,735,892 | A | 4/1998 | Myers et al. |
| 5,744,958 | A | 4/1998 | Werne |
| 5,753,251 | A | 5/1998 | Burrell et al. |
| 5,762,615 | A | 6/1998 | Weier |
| 5,766,710 | A | 6/1998 | Turnlund et al. |
| 5,770,255 | A | 6/1998 | Burrell et al. |
| 5,810,870 | A | 9/1998 | Myers et al. |
| 5,843,289 | A | 12/1998 | Lee et al. |
| 5,902,317 | A | 5/1999 | Kleshinski et al. |
| 5,908,409 | A | 6/1999 | Rinehart et al. |
| 5,925,038 | A | 7/1999 | Panescu et al. |
| 5,925,075 | A | 7/1999 | Myers et al. |
| 5,945,153 | A | 8/1999 | Dearnaley |
| 5,951,586 | A | 9/1999 | Berg et al. |
| 5,957,903 | A | 9/1999 | Mitzaee et al. |
| 6,017,553 | A | 1/2000 | Burrell et al. |
| 6,043,451 | A | 3/2000 | Julien et al. |
| 6,096,175 | A | 8/2000 | Roth |
| 6,113,557 | A * | 9/2000 | Fagan et al. ................. 600/585 |
| 6,139,511 | A * | 10/2000 | Huter et al. ................. 600/585 |
| 6,174,329 | B1 | 1/2001 | Callol et al. |
| 6,183,420 | B1 | 2/2001 | Douk et al. |
| 6,203,732 | B1 | 3/2001 | Clubb et al. |
| 6,238,686 | B1 | 5/2001 | Burrell et al. |
| 6,319,277 | B1 | 11/2001 | Rudnick et al. |
| 6,322,588 | B1 | 11/2001 | Ogle et al. |
| 6,325,824 | B2 | 12/2001 | Limon |
| 6,342,067 | B1 | 1/2002 | Mathis et al. |
| 6,432,116 | B1 | 8/2002 | Callister et al. |
| 6,436,132 | B1 | 8/2002 | Patel et al. |
| 6,447,478 | B1 | 9/2002 | Maynard |
| 6,471,721 | B1 | 10/2002 | Dang |
| 6,527,919 | B1 | 3/2003 | Roth |
| 6,533,905 | B2 | 3/2003 | Johnson et al. |
| 6,537,310 | B1 | 3/2003 | Palmaz et al. |
| 6,605,111 | B2 | 8/2003 | Bose et al. |
| 6,610,046 | B1 | 8/2003 | Usami et al. |
| 6,627,246 | B2 | 9/2003 | Mehta et al. |
| 6,645,243 | B2 | 11/2003 | Vallana et al. |
| 6,660,032 | B2 | 12/2003 | Klumb et al. |
| 6,666,882 | B1 | 12/2003 | Bose et al. |
| 6,726,993 | B2 | 4/2004 | Teer et al. |
| 6,755,794 | B2 | 6/2004 | Soukup |
| 6,786,920 | B2 | 9/2004 | Shannon et al. |
| 6,805,898 | B1 | 10/2004 | Wu et al. |
| 7,182,735 | B2 * | 2/2007 | Shireman et al. ............ 600/585 |
| 2001/0009980 | A1 * | 7/2001 | Richardson et al. ......... 600/585 |
| 2001/0020182 | A1 | 9/2001 | Klumb et al. |
| 2001/0039449 | A1 | 11/2001 | Johnson et al. |
| 2002/0032478 | A1 | 3/2002 | Boekstegers et al. |
| 2002/0038143 | A1 | 3/2002 | McCrea et al. |
| 2002/0111667 | A1 | 8/2002 | Girton et al. |
| 2002/0151958 | A1 | 10/2002 | Chuter |
| 2003/0004567 | A1 | 1/2003 | Boyle et al. |
| 2003/0066533 | A1 | 4/2003 | Loy |
| 2003/0088187 | A1 * | 5/2003 | Saadat et al. ................. 600/547 |
| 2004/0098094 | A1 | 5/2004 | Boyle et al. |
| 2004/0111044 | A1 * | 6/2004 | Davis et al. ................. 600/585 |
| 2004/0143288 | A1 | 7/2004 | Searle |
| 2005/0197597 | A1 | 9/2005 | Douk |

FOREIGN PATENT DOCUMENTS

| | | |
|---|---|---|
| EP | 0641224 B1 | 8/1998 |
| EP | 1099004 A1 | 7/1999 |
| EP | 0824900 B1 | 4/2003 |
| EP | 1426071 | 6/2004 |
| EP | 01099004 B1 | 9/2004 |
| GB | 2331998 A | 6/1999 |
| WO | 9307924 A1 | 4/1993 |
| WO | 9323092 A1 | 11/1993 |
| WO | 9425637 A1 | 11/1994 |
| WO | 9513704 A1 | 5/1995 |
| WO | 9726026 A2 | 7/1997 |
| WO | 9966966 A1 | 12/1999 |
| WO | 0004204 A1 | 1/2000 |

OTHER PUBLICATIONS

Boston Scientific, Synchro Microfabricated Nitinol Guidewires, Printout Dec. 9, 2005, bostonscientific.com.

Spine; Hellier, Hedman, Kostuik; Wear Studies for development of an intervertebral disc prosteses; Jun. 1992; US.

Biomaterials; Li; Behaviour of titanium and titania-based ceramics in vitro and in vivo; Feb. 2003; US.

Elsevier; Banks et al.; Ion bombardment modification of surfaces in biomedical applications; 399-434; 1984; Netherlands.

Advances in Bioengineering; Chung, Chang, Han; Development of thin metal film deposition process for the intravascular catheter; Conference; Nov. 14, 1999; US.

Journal of Materials Processing Technology; Kola, Daniels, Cameron, Hashmi; Magnetron suputtering of TiN protective coatings for medical applications; 422-430; Jan. 1996; Ireland.

Journal of Biomedical Materials Research; Yuhta et al.; Blood compatibility of sputter deposited alumina films; 271-224; Feb. 1994.

Society for Biomaterials; Ong, Lucas, Lacefield, Rigney; Properties of calcium-phosphate coatings produced by ion-beam sputter deposition; Conference; May 1, 1991; US.

Asaio; Zabetakis, Cotell, Chrisey, Auyeung; Pulsed laser deposition of thin film hydroxyapatite. Applications for flexible catheters; 896-899; Jul. 1994; US.

European Search Report for European patent application No. 06256409.1, dated Nov. 9, 2007.

* cited by examiner

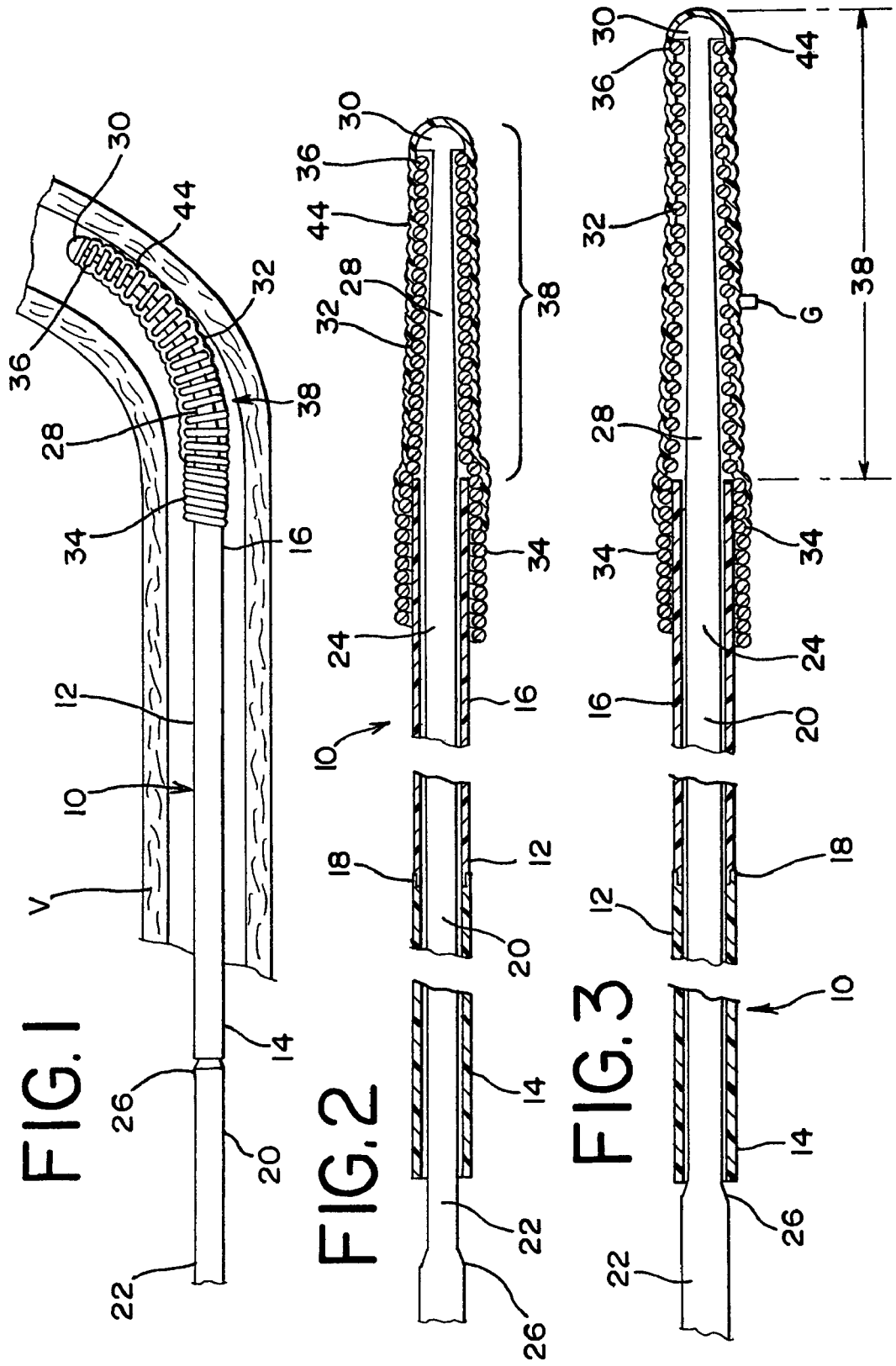

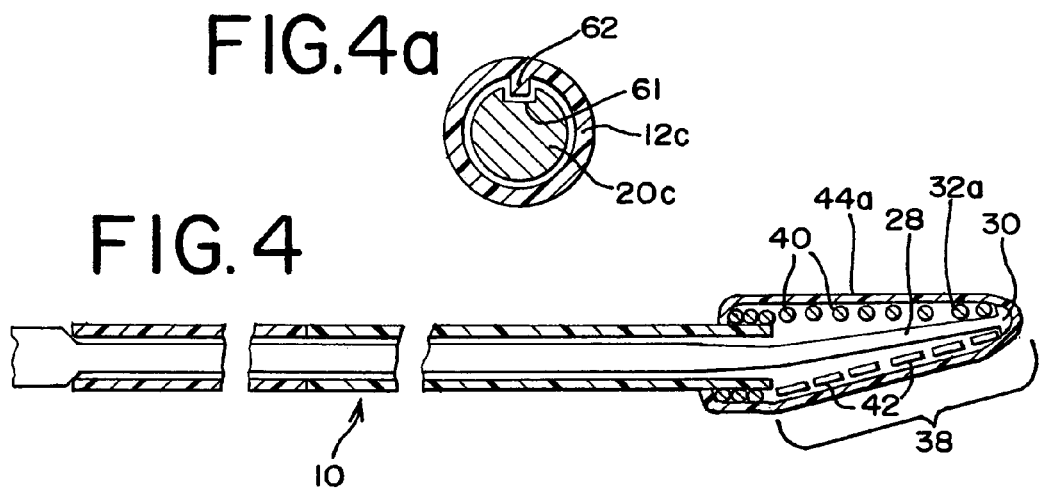
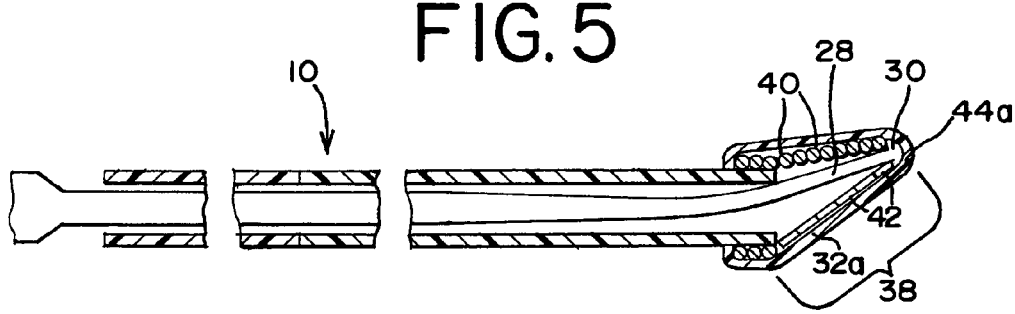
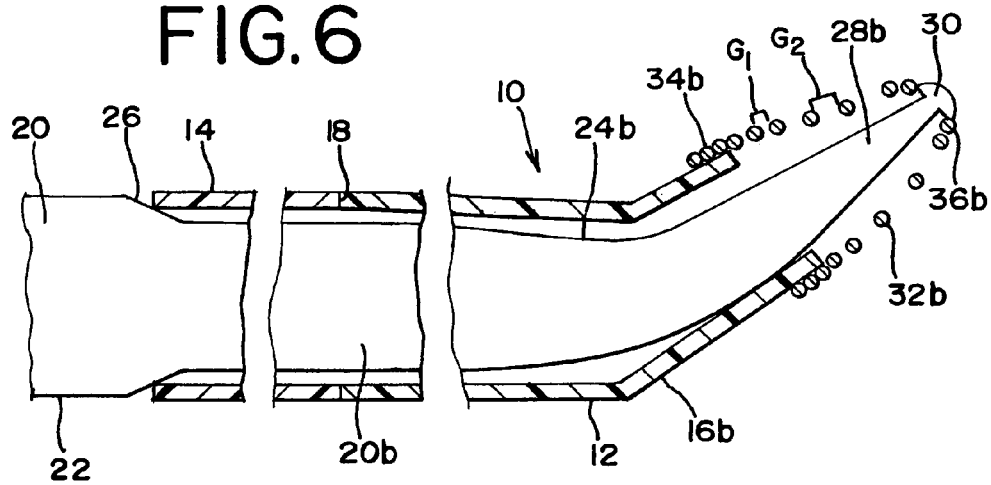

VARIABLE STIFFNESS GUIDEWIRE

FIELD OF THE INVENTION

This invention generally relates to medical devices that are navigable through body vessels of a human subject. More particularly, this invention relates to guidewires used to position a catheter or the like within a body vessel.

DESCRIPTION OF RELATED ART

Vessel defects, such as blockages and stenoses, within the human vasculature system are often treated by the intraluminal delivery of treatment fluids or expansion devices and stents. Expansion devices can take any of a number of forms, but are all generally delivered by a flexible catheter that, once properly positioned, deploys the expansion device. The path to the diseased site is typically tortuous and may additionally pass through other constricted lumens, so catheters cannot be used to define their own path through the vasculature. As such, a more rigid guidewire is first passed through the vasculature to the desired site, and then the catheter is passed over the guidewire.

The different body environments in which guidewires must operate create several design complications. For example, it is desirable for the guidewire to be somewhat flexible so that it can pass through tortuous portions of the vasculature. On the other hand, it is also desirable for the guidewire to be somewhat rigid so that it may be forced through constricted body vessels and lesions or used to perforate the fibrocalcific cap of chronic total coronary artery occlusions. More rigid guidewires also provide tactile feedback to the operator. Most guidewires have a fixed stiffness, so the surgeon must select a guidewire based on the predicted body environment. Of course, if the guidewire is not properly selected, then multiple guidewires with different stiffness values must be used. Even proper guidewire selection cannot obviate the need for multiple guidewire usage for some body environments.

In recognition of this problem, a number of variable stiffness guidewires and stylets have been suggested. Examples can be seen in U.S. Pat. No. 3,854,473 to Matsuo; U.S. Pat. No. 4,215,703 to Wilson; U.S. Pat. No. 5,762,615 to Weier; U.S. Pat. No. 5,957,903 to Mirzaee et al.; U.S. Pat. No. 6,113,557 to Fagan et al; U.S. Pat. No. 6,183,420 to Douk et al.; and U.S. Pat. No. 6,755,794 to Soukup, all of which are hereby incorporated herein by reference.

Generally speaking, these variable stiffness devices include a tube which receives a corewire that protrudes distally beyond the tube. A coiled spring surrounds the protruding portion and is connected at opposite ends to the corewire and the tube, such that axial movement of the corewire with respect to the tube will compress or stretch the spring. When the tip of the corewire is moved away from the tube using a handle outside of the body, the separation gaps between the coils of the spring enlarge and the tip become more flexible and better suited for being fed through tortuous body vessels. In the event that the guidewire encounters a constricted body vessel through which it must pass, the corewire is moved toward the tube, which compresses the spring and causes the separation gaps to diminish and the tip to become more rigid.

While these known variable stiffness guidewires are an improvement over previous fixed stiffness guidewires, there are still several possible areas of improvement. For example, the described tubes are comprised of a relatively rigid material, typically stainless steel. Stainless steel is well-suited for procedures requiring the guidewire to be forced through a constricted vessel, but it is not sufficiently flexible for procedures requiring the guidewire to define a tortuous path.

Another problem with known variable stiffness guidewires is that they use springs having a uniform cross-sectional shape. Most often, the coil spring has a round or circular cross-sectional shape, which performs well for operations requiring flexibility, but not as well for operations requiring more stiffness. The other known alternative is to use a flat coil spring, which is typically stronger than a spring having a round cross-sectional shape and performs better in operations requiring a relatively stiff guidewire tip. However, flat coil springs are not as flexible as would be desired in operations involving a tortuous vessel pathway.

Accordingly, a general aspect or object of the present invention is to provide a variable stiffness guidewire having a tube which provides increased flexibility without sacrificing stiffness.

Another aspect or object of this invention is to provide a guidewire with a spring having regions of differing stiffness.

Other aspects, objects and advantages of the present invention, including the various features used in various combinations, will be understood from the following description according to preferred embodiments of the present invention, taken in conjunction with the drawings in which certain specific features are shown.

SUMMARY OF THE INVENTION

In accordance with one aspect of the present invention, a variable stiffness guidewire is provided with a tube, an elongated corewire received by the tube and protruding from both ends of the tube, and a coiled spring surrounding the distally protruding portion of the corewire. The corewire is movable with respect to the tube in order to compress or stretch the spring, which contributes to varying the stiffness of the tip of the guidewire. The tube has a composite structure, wherein a proximal portion is relatively rigid and a distal portion is more flexible. In a preferred embodiment, the proximal portion is stainless steel and the distal portion is comprised of a shape memory material, such as a nitinol material. A tube according to the present invention is sufficiently rigid to be pushed through constricted vessels and the like, but also has a more flexible distal portion for pre-shaping and improved navigability through tortuous body vessels.

According to another aspect of the present invention, a spring is provided for use with a guidewire. The spring has different cross-sectional shapes at different locations. In a preferred embodiment, selected sections of the spring are substantially flat for providing improved stiffness and tip shape retention during stiffening. Other sections of the spring have a substantially round or circular cross-sectional area for improved bending flexibility. The pitch and/or length of the spring may be varied in order to impart different performance characteristics, as dictated by the subject body environment.

Special application for the present invention has been found for guidewire delivery of catheters to vessels of the human vascular system. However, the present invention is also applicable to guidewire delivery of catheters to other body lumens, such as in gastrointestinal procedures, so it will be understood that the products described herein are not limited to particular medical devices or particular surgical applications.

BRIEF DESCRIPTION OF THE DRAWINGS

FIG. 1 is a front elevational view of a guidewire according to an aspect of the present invention, shown at a typical in-use location;

FIG. 2 is a cross-sectional view of the guidewire of FIG. 1, in a maximum stiffness configuration;

FIG. 3 is a cross-sectional view of the guidewire of FIG. 1, in a minimum stiffness configuration;

FIG. 4 is a cross-sectional view of a guidewire according to another aspect of the present invention, in a minimum stiffness configuration;

FIG. 4a is a transverse cross-sectional view through a guidewire embodiment having a non-rotation feature;

FIG. 5 is a cross-sectional view of the guidewire of FIG. 4, in a maximum stiffness configuration; and FIG. 6 is a cross-sectional view of another embodiment of a guidewire according to the present invention.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 illustrates a guidewire 10 in a body vessel V. The guidewire 10 includes a hypotube or tube 12 with a proximal portion 14 and a distal portion 16, which are best shown in FIGS. 2 and 3. The proximal portion 14 and distal portion 16 are made of different materials, typically being separate tubes that are joined at joint 18. The respective proximal and distal portions 14 and 16 preferably have substantially equal respective outer and inner diameters at their location of contact, which facilitates the creation of a smooth joint 18. The joint 18 is preferably smooth or atraumatic in order to prevent damage to the surrounding vessel V, corewire 20, or to a catheter slid over the guidewire 10.

The proximal and distal portions 14 and 16 are comprised of different materials, because they serve different functions. The proximal portion 14 extends from the joint 18 to outside of the body and is manipulated by the operator to feed the guidewire 10 through the vasculature. Accordingly, it is preferable for the proximal portion 14 to be made of a relatively rigid, biocompatible material. In a preferred embodiment, the proximal portion 14 is comprised of stainless steel.

In contrast to the proximal portion 14, it is important for the distal portion 16 to be relatively flexible in order to follow the vasculature path, especially if the path is tortuous. Furthermore, it is often useful to pre-shape the distal portion 16 in anticipation of the body environment, so the distal portion 16 should be suitable for repeated shaping without weakening, permanent deformation, or failure. Accordingly, the distal portion 16 is preferably made of a material having shape memory properties. When used herein, the term "shape memory" is intended to refer to materials capable of recovering from an apparent inelastic deformation and returning to a default geometry. In a preferred embodiment, the distal portion 16 is made of a nitinol material having a tubular default geometry illustrated in FIGS. 1-3. Of course, the distal portion 16 may have any other default geometry without departing from the scope of the present invention. An example is a curved or bent geometry, as illustrated in FIG. 6, of a distal portion 16b. A curved or bent protruding portion 28b of the distal end 24b of a corewire 20b also is shown.

The distal portion 16 is most preferably made of a nitinol composition having a transformation temperature greater than body temperature, such that the nitinol material is in a martensitic state at room temperature and when in vivo. In use, the austenitic shape of the distal portion 16 is heat treated and initially set to the substantially tubular shape of FIGS. 1-3. Thereafter, the distal portion 16 is brought below the heat treatment temperature and to a temperature below the transformation temperature. For example, when not in use, the distal portion 16 will typically be stored in a martensitic state at room temperature. When the guidewire 10 is to be used, the operator may pre-shape the distal portion 16 to a generally curved configuration that would be useful in navigating the anticipated path. After the operation, the distal portion 16 may be heated above the transformation temperature in order to reset it to the default geometry.

The nature of the joint 18 depends on the materials used to form the proximal and distal portions 14 and 16. Mechanical methods, such as crimping or swaging, are typically the most reliable ways to join the proximal and distal portions 14 and 16. Welding, brazing, and soldering may also be used, but special care must be taken to remove the oxide layer when practicing such methods with nitinol. The shape memory properties of nitinol and similar materials may be exploited by expanding or contracting the martensitic distal portion 16, then returning it to its austenitic state to tightly engage the proximal portion 14. Other joining methods are possible and it is well within the skill of one in the art to select an appropriate method.

The tube 12 movably receives an elongated corewire 20 extending between a proximal end 22 and a distal end 24. The corewire 20 is generally constructed in accordance with known devices and may be made of stainless steel or, most preferably, a nitinol material. Other materials and combinations of materials, such as a stainless steel proximal end and a nitinol material distal end, are also possible. Furthermore, rather than using a single corewire, it is instead possible to use a plurality of smaller corewires for improved flexibility.

The proximal end 22 of the corewire 20 terminates in a handle, not illustrated, that remains outside of the body for manipulation by an operator, as will be described herein. Intermediate the handle and the proximal portion 14 of the tube 12 is a tapered stopping mechanism or diameter ramp-up 26. The stopping mechanism 26 has a larger diameter than the tube inner diameter, so it limits distal or downstream movement of the corewire 20 with respect to the tube 12 by coming into contact with the proximal portion 14. Downstream movement of the corewire 20 can be understood by comparing FIG. 2 to FIG. 3, while proximal or upstream movement can be understood as moving the corewire 20 from the orientation of FIG. 3 to the orientation of FIG. 2.

The distal end 24 of the corewire 20 includes a tapered protruding portion 28 that extends at least partially beyond the distal portion 16 of the tube 12 and terminates at an atraumatic weld 30. The protruding portion 28 is tapered in order to increase its flexibility for improved navigability through tortuous body cavities. At least the protruding portion 28 of the corewire 20 is preferably made of a nitinol or another material having shape memory properties in order to allow for repeatable pre-shaping without weakening the corewire 20. FIGS. 4 and 5 provide another example of a pre-shaped protruding portion 28.

The protruding portion 28 is surrounded by a coiled spring 32 that extends from the distal portion 16 of the tube 12 to the weld 30 of the corewire 20. Preferably, a proximal end 34 of the spring 32 is connected to the distal portion 16 and a distal end 36 of the spring 32 is connected to the weld 30, such that the spring 32 is movable with the tube 12 and with the corewire 20 between the maximum stiffness configuration of FIG. 2 and the minimum stiffness configuration of FIG. 3.

In the maximum stiffness configuration, there is preferably no separation gap between adjacent coils. This configuration imparts increased stiffness to the guidewire tip 38. When used herein, the term "tip" or "guidewire tip" refers to the protruding portion 28 of the corewire 20 and any other component extending beyond the distal portion 16 of the tube 12, such as the portion of the spring 32 surrounding the protruding portion 28. The separation gap G between adjacent coils is preferably about 0.010 inch in the minimum stiffness configuration of FIG. 3, which gap decreases the stiffness of the tip 38. The maximum stretching of the spring 32 is regulated by the location of the diameter ramp-up 26 at the proximal end 22 of the corewire 20, which contacts the tube proximal portion 14 to prevent further downstream movement.

The corewire 20 is preferably axially slideable with respect to the tube 12, but other modes of axial advancement, such as rotation, are within the scope of the present invention. Typically, the spring 32 is also rotatably mounted to at least one of the distal portion 16 and/or weld 30, which allows the corewire 20 to be rotated with respect to the tube 12 without torsional resistance from the spring 32. Alternatively, a non-rotation feature can be included, such as by incorporating a longitudinal pathway such as a flat slot or channel 61 along corewire 20c and a complementary protrusion or follower 62 of tube 12c, as shown in FIG. 4a. Instead, the pathway can be along the tube and the protrusion on the corewire.

The guidewire 10 is preferably provided with a ratcheting or locking mechanism, not illustrated, associated with the handle in order to allow controlled movement of the corewire 20 with respect to the tube 12 and/or to prevent unintentional movement of the corewire 20 with respect to the tube 12. A suitable mechanism is illustrated in U.S. Pat. No. 3,854,437 to Matsuo, which is hereby incorporated herein by reference. Of course, other mechanisms are possible and within the scope of the present invention.

The spring 32 of FIGS. 1-3 is illustrated as having a round or circular cross-sectional shape, but other shapes, such as a flat coiled spring, are within the scope of the present invention. According to an aspect of the present invention, shown in FIGS. 4 and 5, the spring 32a has a heterogeneous combination of cross-sectional shapes, which promotes bending flexibility and curvature. The embodiment of FIGS. 4 and 5 includes a single spring 32a with a cross-section that varies between a substantially circular or round shape 40 and a substantially flat or rectangular shape 42. The respective round and flat shapes 40 and 42 have different properties, which can be used for enhanced performance, as will be described herein. Regardless of the cross-sectional shape of the coils, the spring may have a varying pitch along its length in order to provide differing flexibility characteristics. For example, FIG. 6 shows a spring 32b having an increasing pitch; that is, the separation gap increases from $G_1$ to $G_2$ and from the proximal end 34b to the distal end 36b of the spring.

The spring is preferably surrounded by a sheath 44 of lubricating and/or sealing material. Typically, the sheath 44 is more lubricious than the spring 32. The spring is made of any suitable guidewire spring material, preferably a material that is radiopaque, typically by being a high density metal. Spring materials include platinum, tungsten, and alloys such as tungsten iridium alloys, as well as stainless steel. Also, the sheath 44 preferably is fluid-tight and prevents body fluids, contrast dye, and the like from seeping into the interior of the guidewire 10. In a preferred embodiment, the sheath 44 is polytetrafluoroethylene (PTFE), which is heat-shrunk over the spring 32 and weld 30. A similar sheath 44a is illustrated for encapsulating spring 32a.

In use, the guidewire tip 38 and/or distal portion 16 of the tube 12 are pre-shaped by the operator, if necessary, in anticipation of the expected body environment. If the tip 38 is to be pre-shaped, then the guidewire embodiment of FIGS. 4 and 5 can be provided to enhance the preshaping action. As illustrated, the round sections 40 of the spring 32a may be diametrically opposed by the flat sections 42, which causes the spring 32a to better conform to the pre-shaped protruding portion 28 in the compressed or maximum stiffness configuration of FIG. 5, due to the greater length of the flat sections 42. Such flat sections that are illustrated have a greater axial length than the illustrated round sections, and are thereby less bendable. Also, this effect is achieved because the gap between same is less than the gap between the coils with a round cross-section. Alternative distributions of round and flat spring sections 40 and 42, such as alternating adjacent round and flat sections, may be employed for different performance characteristics and it is to be understood that the illustrated embodiment of FIGS. 4 and 5 only shows one possible spring configuration. Generally, the less rigid the section, whether by shape, size or material, the easier for the spring and thus the tip to flex and typically bend to follow a change in shape of the vessel through which it is fed.

When the guidewire 10 has been pre-shaped, it is then inserted into a body vessel through an incision in the skin. The guidewire 10 may be inserted with the tip 38 in a maximum stiffness or minimum stiffness configuration, or in an intermediate stiffness configuration, depending on the expected body environment. The guidewire 10 is fed through the vasculature and may be adjusted to a stiffer tip configuration for constricted vessel sites and to a more flexible tip configuration for twisting and tortuous sites. Of course, this is only an exemplary method of using a guidewire according to the present invention and should not be considered limiting.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A variable stiffness guidewire for navigating through body vessels, comprising:

a tube having a proximal portion substantially comprised of a first material and a distal portion substantially comprised of a second material, wherein said second material is different from and more flexible at human body temperature than said first material;

an elongated corewire received by the tube and including a distal end, a proximal end, and a protruding portion extending beyond the distal portion of the tube;

a unitary coiled spring surrounding at least said protruding portion of said corewire, said spring having a distal end associated with said distal end of said corewire and a proximal end associated with said distal portion of said tube, wherein said corewire is axially movable with respect to said tube to adjust the total length of the spring and thus the stiffness of said spring;

the unitary coiled spring having a plurality of cross-sectional shapes, wherein a plurality of coil lengths of the spring have a first portion with a first cross-sectional shape that is substantially flat and a second portion with a second cross-sectional shape that is substantially circular with a given diameter, said substantially flat first cross-sections are diametrically opposed to said substantially circular second cross-sections, the first cross-sections being along a first longitudinal side of the coiled spring that is diametrically opposed to a second longitudinal side of the unitary coiled spring, and said substantially flat first cross-sections each have a length and a width shorter than the length, and said length extends substantially parallel to said corewire at its said protruding portion, said substantially parallel length being greater than the given diameter of said substantially circular second cross-sections, the second longitudinal side being longer than the first longitudinal side when respective flat first cross-section widths and circular second cross-sections of adjacent coil lengths engage each other, whereby the unitary coiled spring exhibits pre-shaped curvature bending; and a non-rotation system comprising a longitudinal pathway along one of said tube or corewire and a follower on the other of said tube or corewire, said follower being slidable with respect to said pathway and at least partially received within the pathway.

2. The guidewire of claim 1, wherein said second material has shape memory properties.

3. The guidewire of claim 1, wherein said second material is a nitinol material.

4. The guidewire of claim 1, wherein said first material is stainless steel and said second material is a nitinol material.

5. The guidewire of claim 4, wherein said proximal end of said corewire includes a portion having an increased diameter for contacting said proximal portion of said tube to prevent downstream movement of said corewire with respect to said tube.

6. The guidewire of claim 4, wherein said distal end of said spring is connected to and movable with said distal end of said corewire and wherein said proximal end of said spring is connected to and movable with said distal portion of said tube.

7. The guidewire of claim 6, further comprising a separation gap between adjacent coils of said spring and wherein downstream movement of said corewire with respect to said tube generally increases the separation gap to thereby decrease the stiffness of the coil, and wherein upstream movement of said corewire with respect to said tube generally decreases the separation gap to thereby increase the stiffness of the coil.

8. The guidewire of claim 7, wherein said separation gap is variable between approximately 0 inches in a maximum stiffness configuration and approximately 0.010 inch in a minimum stiffness configuration.

9. The guidewire of claim 1, further comprising an atraumatic weld associated with said distal end of said corewire.

10. The guidewire of claim 1, further comprising a plurality of corewires receivable by said tube.

11. The guidewire of claim 1, wherein at least a portion of said corewire is shapeable.

12. The guidewire of claim 1, wherein at least a portion of said distal portion of said tube is shapeable.

13. The guidewire of claim 1, wherein said spring has a varying pitch.

14. The guidewire of claim 1, further comprising a sheath covering said protruding portion of said corewire.

15. The guidewire of claim 14, wherein said sheath is heat-shrunk over said spring for providing a fluid-tight seal.

16. The guidewire of claim 1, wherein the stiffness of the spring is variable by changing said length.

17. The guidewire of claim 16, wherein said length is varied by axially moving the corewire with respect to the tube.

18. The guidewire of claim 16, wherein said proximal end of the spring is engageable with the distal portion of the tube and said distal end of the spring is engageable with the corewire.

19. The guidewire of claim 1, further comprising a separation gap between adjacent coils, wherein the separation gap is approximately 0 inches in a maximum stiffness configuration and the separation gap is approximately 0.10 inch in a minimum stiffness configuration.

20. The guidewire of claim 1, wherein the spring has a varying pitch.

21. The guidewire of claim 1, wherein said substantially flat cross-sections and said substantially circular cross-sections are arranged in an alternating pattern.

22. The guidewire of claim 1, wherein said second material is transformable between an austenitic state and a martensitic state and wherein said proximal and distal portions of the tube are connected at a joint formed by transforming the distal portion from the martensitic state to the austenitic state to engage the proximal portion.

23. A variable stiffness guidewire for navigating through body vessels, comprising:

a tube having a proximal portion substantially comprised of a first material and a distal portion substantially comprised of a second material transformable between an austenitic state and a martensitic state, wherein said proximal and distal portions are connected at a joint formed by transforming the distal portion from the martensitic state to the austenitic state to engage the proximal portion;

an elongated corewire received by the tube and including a distal end, a proximal end, and a protruding portion extending beyond the distal portion of the tube;

a unitary coiled spring surrounding at least said protruding portion of said corewire, said spring having a distal end associated with said distal end of said corewire and a proximal end associated with said distal portion of said tube, wherein said corewire is axially movable with respect to said tube to adjust the total length of the spring and thus the stiffness of said spring; and the unitary coiled spring having a plurality of cross-sectional shapes, wherein a plurality of coil lengths of the spring have a first portion with a first cross-sectional shape that is substantially flat and a second portion with a second cross-sectional shape that is substantially circular with a given diameter, said substantially flat first cross-sections are diametrically opposed to said substantially circular second cross-sections, the first cross-sections being along a first longitudinal side of the coiled spring that is diametrically opposed to a second longitudinal side of the unitary coiled spring, and said substantially flat first cross-sections each have a length and a width shorter than the length, and said length extends substantially parallel to said corewire at its said protruding portion, said substantially parallel length being greater than the given diameter of said substantially circular second cross-sections, the second longitudinal side being longer than the first longitudinal side when respective substantially flat cross-section widths and substantially circular second cross-sections of adjacent coil lengths engage each other, whereby the unitary coiled spring exhibits pre-shaped curvature bending, engage each other.

24. The guidewire of claim 23, wherein the distal portion of the tube engages an outer surface of the proximal portion of the tube at the joint.

25. The guidewire of claim 23, wherein the distal portion of the tube engages an inner surface of the proximal portion of the tube at the joint.

26. The guidewire of claim 1, wherein said follower comprises an inward radial projection of the tube and said pathway comprises a channel defined in the corewire.

27. The guidewire of claim 1, where said non-rotation system is configured to allow the corewire to be received by the tube in only one angular orientation.

* * * * *